(12) United States Patent
Tao et al.

(10) Patent No.: US 12,082,909 B2
(45) Date of Patent: Sep. 10, 2024

(54) INTRAORAL SCANNER WITH A SCANNING REFLECTOR AND A METHOD FOR CALIBRATION OF A SCANNING REFLECTOR

(71) Applicant: Dental Imaging Technologies Corporation, Atlanta, GA (US)

(72) Inventors: Xiaodong Tao, Rochester, NY (US); Chuanmao Fan, Rochester, NY (US)

(73) Assignee: DENTAL IMAGING TECHNOLOGIES CORPORATION, Quakertown, PA (US)

( * ) Notice: Subject to any disclaimer, the term of this patent is extended or adjusted under 35 U.S.C. 154(b) by 337 days.

(21) Appl. No.: 17/431,750

(22) PCT Filed: Mar. 11, 2020

(86) PCT No.: PCT/US2020/022201
§ 371 (c)(1),
(2) Date: Aug. 18, 2021

(87) PCT Pub. No.: WO2020/185974
PCT Pub. Date: Sep. 17, 2020

(65) Prior Publication Data
US 2022/0117493 A1    Apr. 21, 2022

Related U.S. Application Data

(60) Provisional application No. 62/817,054, filed on Mar. 12, 2019.

(51) Int. Cl.
*A61B 5/00*    (2006.01)

(52) U.S. Cl.
CPC .......... *A61B 5/0088* (2013.01); *A61B 5/0066* (2013.01); *A61B 2560/0223* (2013.01); *A61B 2562/028* (2013.01)

(58) Field of Classification Search
CPC ................ A61B 5/0088; A61B 5/0066; A61B 2560/0223; A61B 2562/028
See application file for complete search history.

(56) References Cited

U.S. PATENT DOCUMENTS

2008/0024085 A1* 1/2008 Abramovitch ........... G05B 5/01
                                                                318/611
2009/0260113 A1* 10/2009 Rice ..................... G01Q 10/065
                                                                850/33

(Continued)

OTHER PUBLICATIONS

International Preliminary Report on Patentability received for PCT Patent Application No. PCT/US2020/022201, mailed on Sep. 23, 2021, 10 pages.

(Continued)

*Primary Examiner* — Sean A Frith
(74) *Attorney, Agent, or Firm* — Alston & Bird LLP

(57) ABSTRACT

An intraoral scanner (90) is disclosed for use with a dental optical coherence tomography system. The scanner has a scanning reflector that is energizable to direct a scanning beam in a raster pattern toward a sample (S) surface. The scanning reflector is further to direct a reflected beam from the sample surface toward a detector (60). The scanning reflector is calibrated to direct the scanning and reflected beams in an open-loop control mode. A dental optical coherence tomography system and a method for calibration of a scanning reflector are also disclosed.

17 Claims, 10 Drawing Sheets

(56) References Cited

U.S. PATENT DOCUMENTS

| | | | | |
|---|---|---|---|---|
| 2014/0221747 | A1* | 8/2014 | Tearney | A61B 1/04 |
| | | | | 600/109 |
| 2016/0360969 | A1* | 12/2016 | Sumi | A61B 5/4552 |
| 2018/0085002 | A1* | 3/2018 | Glinec | A61C 9/0073 |
| 2018/0317764 | A1* | 11/2018 | Bender | A61B 3/13 |
| 2019/0117075 | A1* | 4/2019 | Fan | A61B 5/0073 |

OTHER PUBLICATIONS

International Search Report and Written Opinion received for PCT Patent Application No. PCT/US2020/022201, mailed on Jul. 31, 2020, 15 pages.

\* cited by examiner

INTRAORAL SCANNER WITH A SCANNING REFLECTOR AND A METHOD FOR CALIBRATION OF A SCANNING REFLECTOR

FIELD OF THE INVENTION

The present invention relates generally to intraoral optical coherence tomography (OCT) imaging and, more particularly, to calibration for open-loop control of an electromechanical scanner apparatus used within a handheld OCT imaging device.

BACKGROUND

Optical coherence tomography (OCT) is a non-invasive imaging technique that employs interferometric principles to obtain high resolution, cross-sectional tomographic images that characterize the depth structure of a sample. Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging.

OCT has been described as a type of "optical ultrasound" imaging reflected energy from within living tissue to obtain cross-sectional data. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus and interference effects are used to determine characteristics of the surface and near-surface underlying structure of the sample. Interference data can be acquired by rapidly scanning the illumination across the sample. At each of several thousand points along the sample surface, the OCT apparatus obtains an interference profile which can be used to reconstruct an A-scan with an axial depth into the material that is a factor of light source coherence. For most tissue imaging applications, OCT uses broadband illumination sources and can provide image content at depths of up to a few millimeters (mm).

Hand-held intraoral scanners for use with dental optical coherence tomography (OCT) systems require a compact, fast two-dimensional (2D) scanner integrated into the intraoral scanning probe. Traditionally, galvanometers have been used in optical scanning systems to provide scanning functionality. More recently, because of their advantages with respect to bulk, weight, and complexity, MEMS-based devices are being used in hand-held optical scanning systems due to their low cost and compact size.

Calibration of the MEMS scanner can be challenging; conventional techniques for calibration can add complexity and cost to the calibration task. For example, solutions that employ low-pass filtering can constrain MEMS bandwidth and performance. The relatively high Q-factor of MEMS devices further complicates the tasks of MEMS scanner calibration and control. More advanced closed-loop operation of MEMS-based devices often requires additional sensors for the generation of feedback signals. The increased complexity and the high cost required for closed-loop operation have thus far limited the use of such MEMS-based scanners in a hand-held device.

Therefore, there is a need in the industry for a compact, fast, two-dimensional (2D) MEMS-based intraoral scanner that solves these and other problems, difficulties, and shortcomings.

SUMMARY

Broadly described, the present invention comprises apparatuses and methods for

According to one example embodiment of the present invention, there is provided an intraoral scanner for use with a dental optical coherence tomography system that comprises a scanning reflector that is energizable to direct a scanning beam toward a surface in a raster pattern and to direct a beam reflected from the surface toward a detector. The scanning reflector is calibrated to direct the scanning and reflected beams in an open-loop control mode.

Various advantages and benefits of the present invention will become apparent from reading the following more particular description of example embodiments thereof and as illustrated in the accompanying drawings.

DETAILED DESCRIPTION OF EXAMPLE EMBODIMENTS

Figure 1:
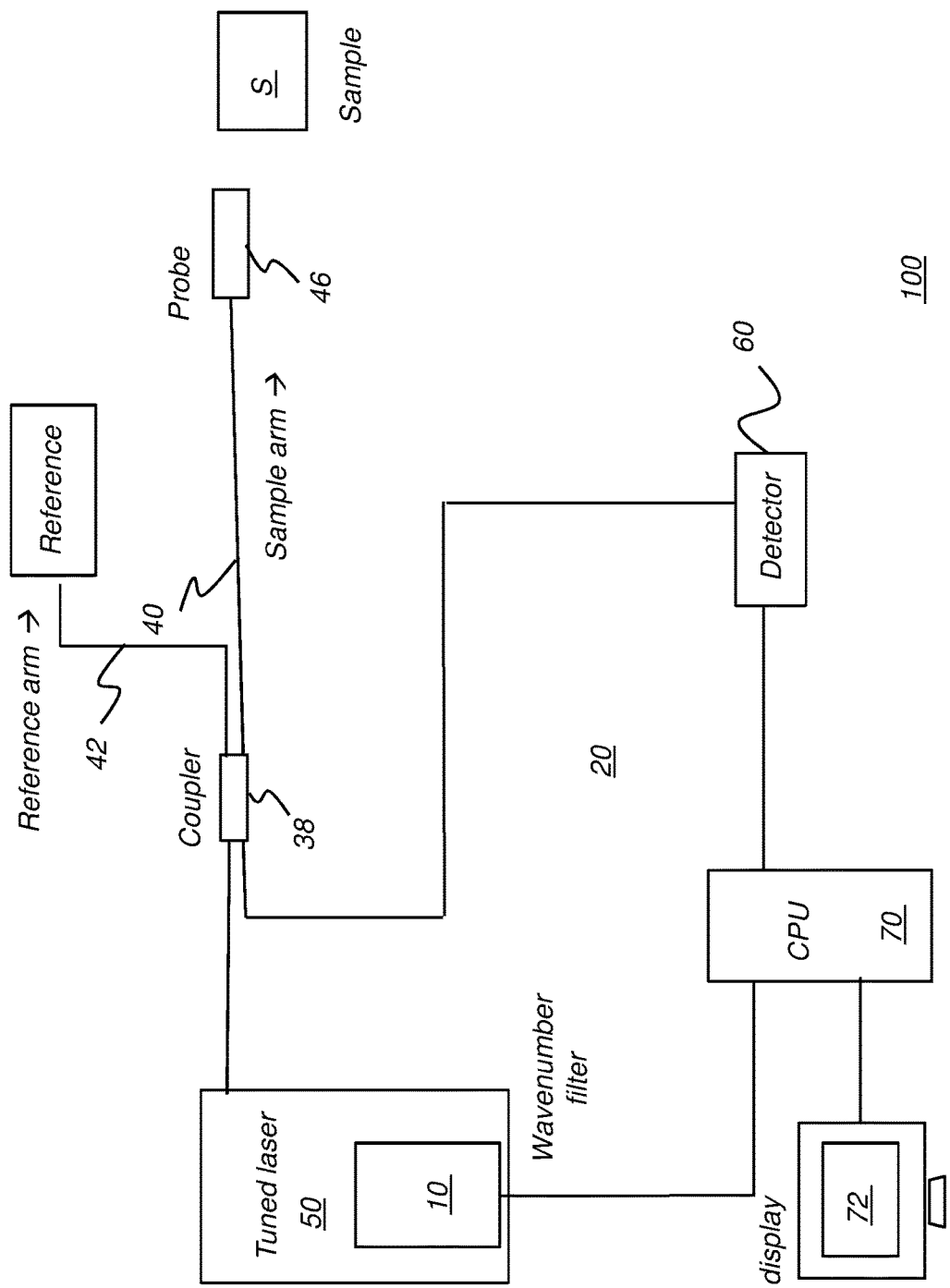
FIG. 1 is a schematic diagram displaying a swept-source OCT (SS-OCT) apparatus according to an example embodiment of the present invention.

The following is a detailed description of example embodiments of the present invention, reference being made to the drawings in which the same reference numerals identify the same elements of structure or steps of a method in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

MEMS reflectors are typically fabricated using semiconductor fabrication technologies, with the dimensions of reflective surfaces used for beam scanning based on beam width and typically ranging from a few hundred micrometers to a few millimeters for hand-held scanning devices, for example. Various structural arrangements are used for reflector implementation and actuation, including the use of arrayed features.

While the description herein provides examples directed to intraoral OCT use, it should be understood and appreciated that the structures, methods, features, and practices described herein can be more generally applied to other types of OCT imaging, including without limitation maxillofacial imaging, and can be particularly advantageous for handheld OCT scanning devices employed in dental or medical applications.

The general term "scanner" relates to an optical system that is energizable to project a scanned light beam of broadband light that is directed to the tooth surface through a sample arm and acquired, as reflected and scattered light returned in the sample arm, for measuring interference with light from a reference arm used in OCT imaging of a surface. According to an example embodiment of the present invention, the scanned light beam uses broadband near-IR (BNIR) light; however, other types of broadband light could alternatively be used. The term "raster scanner" relates to the combination of hardware components that sequentially scan light toward spaced locations along a sample, as described in more detail subsequently.

By way of example, the simplified schematic diagram of FIG. 1 displays the components of one type of OCT apparatus, here, a conventional swept-source OCT (SS-OCT) apparatus 100 using a Michelson interferometer system 20 with a programmable filter 10 that is part of a tuned laser 50. For intraoral or maxillofacial OCT, for example, laser 50 can be tunable over a range of frequencies (wave-numbers k), such as those corresponding to wavelengths between about 300 and 2000 nm, for example. According to an example embodiment of the present invention, a tunable range of about 60 nm bandwidth centered about 1300 nm is used for intraoral OCT.

In the FIG. 1 device, the variable tuned laser 50 output goes through a coupler 38 and to a sample arm 40 and a reference arm 42. The sample arm 40 signal goes to a handpiece or probe 46 for measurement of a sample "S". The reference arm 42 signal is directed by a reference, which can be a mirror or a light guide, through coupler 38 to a detector 60. The detector 60 may use a pair of balanced photodetectors configured to cancel common mode noise.

Control logic processor 70 (also sometimes referred to as "control processing unit CPU 70", "processer 70", or "CPU 70") is in signal communication with tuned laser 50 and its programmable filter 10 and with detector 60. Processor 70 can control the scanning function of probe 46 and store any needed calibration data for obtaining a linear response to scan signals. Processor 70 obtains and processes the output from detector 60. CPU 70 is also in signal communication with a display 72 for command entry and OCT results display.

It should be emphasized that the system embodiment described with reference to FIG. 1 is intended for example only and represents one illustrative type of intraoral OCT architecture. Example embodiments of the present disclosure can be applied to any type of intraoral OCT imaging apparatus or to other hand-held OCT systems, using any of a number of component arrangements and with a variety of interferometry configurations and operational sequences. For example, the dental OCT system that is used may be a time-domain, spectrum-domain, or swept-source system.

Figure 2:
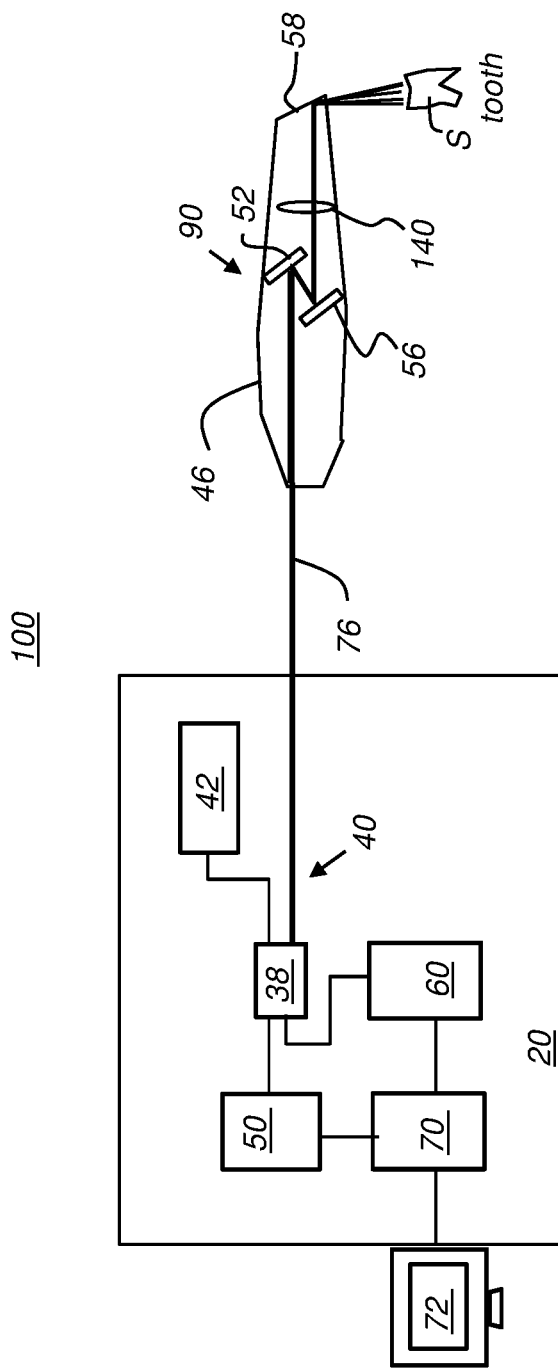
FIG. 2 is a schematic diagram displaying a probe configured for OCT imaging and having a swept-source light source according to an example embodiment of the present invention.

The schematic of FIG. 2 displays an arrangement of OCT apparatus 100 with probe 46 having a scanner 90 for calibration according to an example embodiment of the present invention. In example embodiment of FIG. 2, a fiber cable 76 provides a flexible light path between sample arm 40 of interferometer 20 and probe 46 components. A microelectromechanical systems (MEMS) scanner 52 provides the scanning actuation for directing the swept source light to the surface of sample S, such as a tooth or a calibration target and further for re-directing reflected or scattered light from sample S back to detector 60 within interferometer 20. One or more reflective surfaces 56, 58 can be provided for folding the light path, redirecting light within probe 46 and outward to sample S. Within probe 46 is an objective lens 140 and other optics (not shown) for focus, collimation, and other functions that condition the light to and from the sample.

According to an example embodiment of the present invention, raster scanning by the probe 46 can use any arbitrary scanning pattern to provide uniform or non-uniform spacing of discrete, scanned surface locations. Components of interferometer 20 can be built into probe 46 or may be separately packaged and connected by cable or other connection, such as by a wireless connection.

Figure 3A:
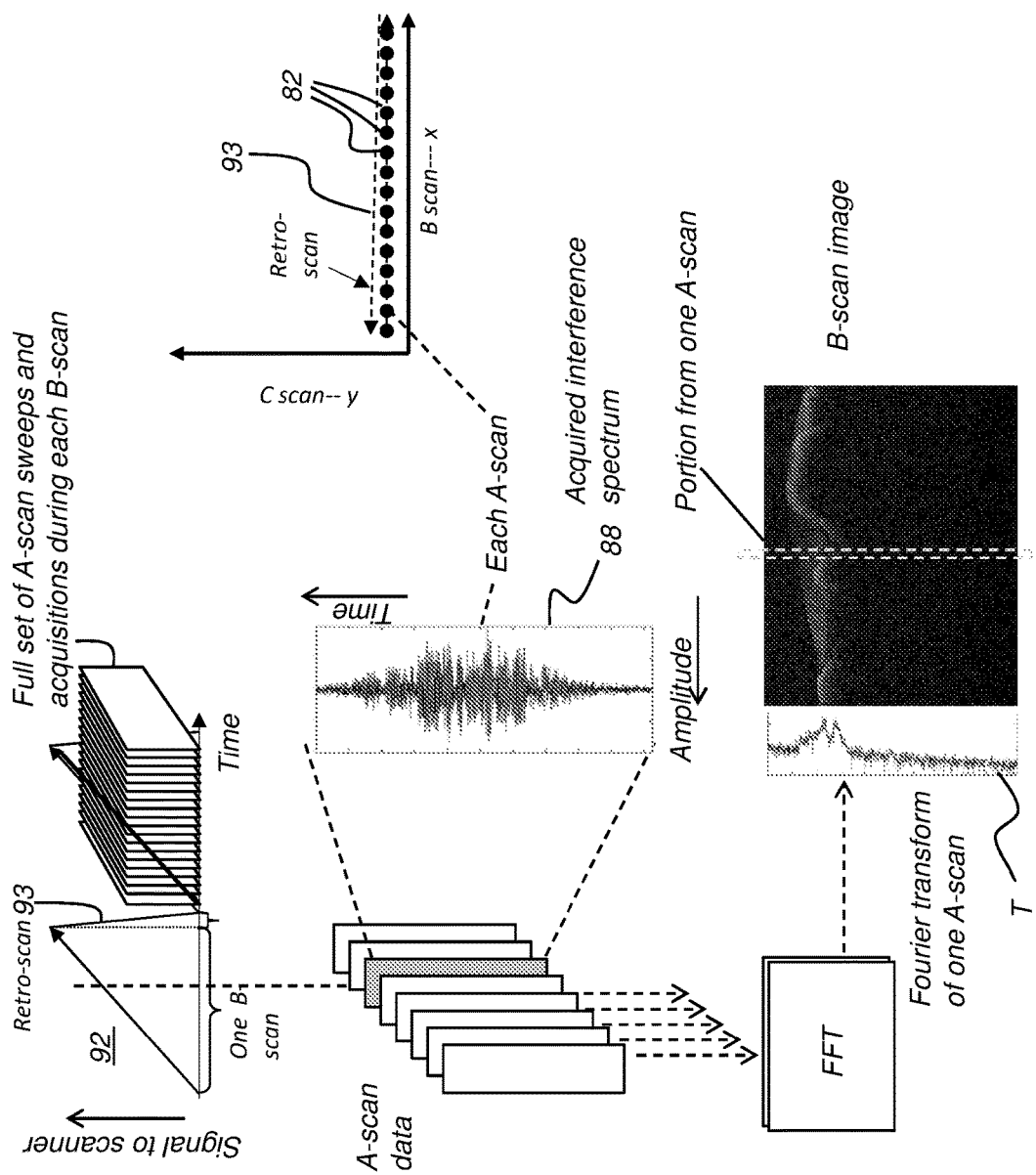
FIG. 3A is a schematic representation displaying a method of scanning operation for obtaining a B-scan.
Figure 3B:
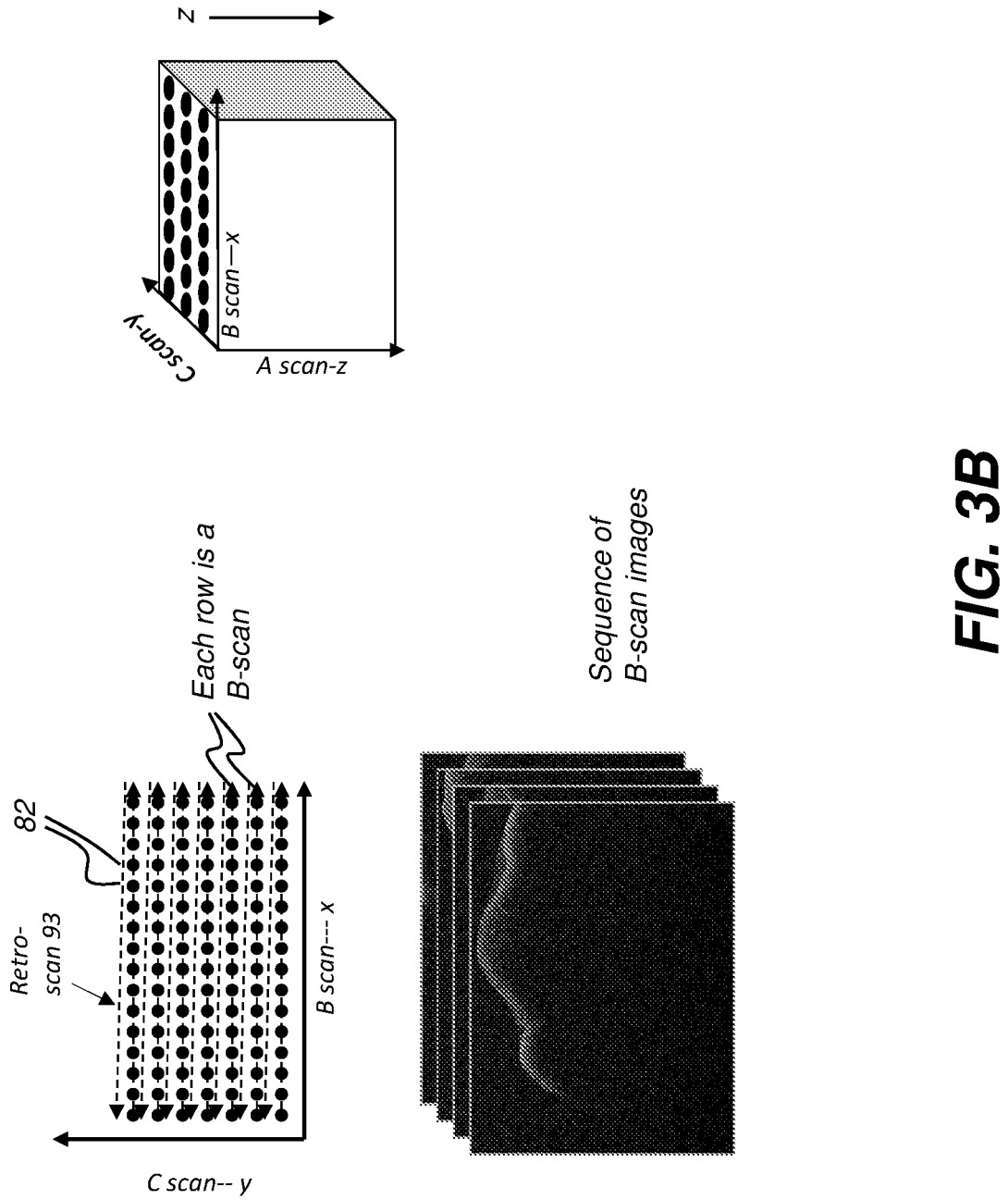
FIG. 3B displays an OCT scanning pattern for C-scan acquisition.

By way of further background, FIGS. 3A and 3B give an overview of the OCT scanning pattern as executed by probe 46 and support components of OCT apparatus 100. FIG. 3A schematically displays the information acquired during each A-scan. The scan signal for obtaining each B-scan image has two linear sections in the example shown, with a scan portion 92, during which the scanning mirror directs the sampling beam from a beginning to an ending position, and a retro-scan 93, during which the scanning mirror is restored to its beginning position. An interference signal 88, shown with DC signal content removed, is acquired over the time interval for each point 82, wherein the signal is a function of the time interval required for the sweep, with the signal that is acquired indicative of the spectral interference fringes generated by combining the light from reference and feedback arms of the interferometer (FIG. 1). The Fast Fourier transform (FFT) generates a transform "T" for each A-scan. One transform signal corresponding to an A-scan is shown by way of example in FIG. 3A.

From the above description, it can be appreciated that a significant amount of data is acquired over a single B-scan sequence. In order to process this data efficiently, a Fast Fourier Transform (FFT) is used, transforming the time-based signal data to corresponding frequency-based data from which image content can more readily be generated.

In Fourier domain OCT, the A scan corresponds to one line of spectrum acquisition which generates a line of depth (z-axis) resolved OCT signal according to the reflected or scattered beam. The B scan data generates a two-dimensional (2-D) OCT image along the corresponding scanned line.

Raster scanning is used to obtain multiple B-scan data by incrementing the raster scanner 90 acquisition in the C-scan (y-axis) direction. This is represented schematically in FIG. 3B, which displays how three-dimensional (3-D) volume information is generated using the A-, B-, and C-scan data.

The wavelength or frequency sweep sequence that is used at each A-scan point 82 can be modified from the ascending or descending wavelength sequence that is typically used. Arbitrary wavelength sequencing can alternately be used. In the case of arbitrary wavelength selection, which may be useful for some particular implementations of OCT, only a portion of the available wavelengths are provided as a result of each sweep. In arbitrary wavelength sequencing, each wavelength can be randomly selected, in arbitrary sequential order, to be used in the OCT system during a single sweep. A-scan points 82 can be uniformly spaced from each other with respect to the x axis, providing a substantially equal x-axis distance between adjacent points 82 along any B-scan image; alternately, spacing can be non-uniform. Similarly, the distance between lines of scan points 82 for each B scan may or may not be uniform with respect to the y axis. X-axis spacing may differ from y-axis spacing; alternately, spacing in x-axis and y-axis directions along these orthogonal axes of the scanned surface may be equal.

According to an example embodiment, nonlinearity of the MEMS-based intraoral scanner can be measured directly from the OCT signal obtained from scanning a calibration target that is configured to verify stability and control of scan spacing. Once the behavior of the scanning components is properly characterized, no additional sensors are required for measurement of the scanner's position. This arrangement simplifies the calibration process and eliminates possible inherent positional error that can be induced by such sensors.

In order to account for possible tolerance-related inaccuracies and performance differences for scanning and support components used for scanning and sensing, the MEMS-based intraoral scanner may be calibrated in position within the handpiece or probe 46. Once calibration is successful, the MEMS mirror can operate in open-loop mode, that is, without requiring sensing or other feedback for controlling the beam scanning action. The scanner's control system can minimize overshoot and oscillation, and can expend the bandwidth over its resonance frequency.

Figure 4:
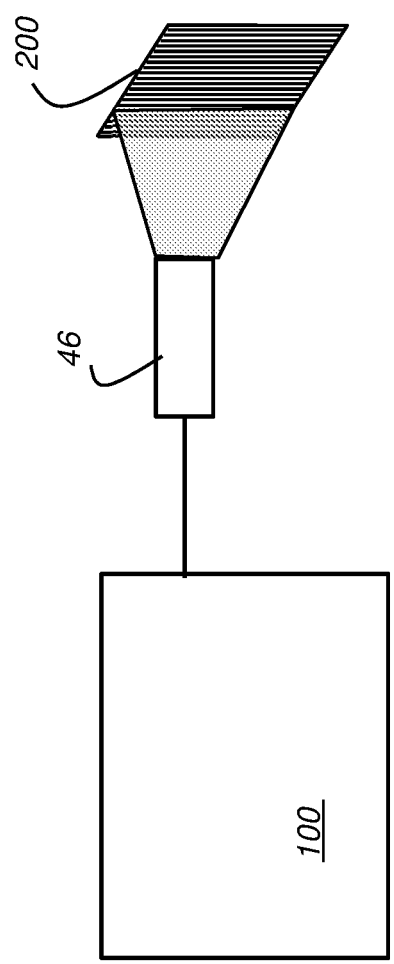
FIG. 4 displays an OCT apparatus setup for scanner calibration according to an example embodiment of the present invention.

The simplified schematic diagram of FIG. 4 displays OCT apparatus 100 set up for scanner calibration according to an example embodiment of the present disclosure. OCT apparatus 100 can be a system fabricated according to the pattern of FIG. 1 or can be some other type of OCT system. According to an example embodiment, the MEMS-based intraoral scanner 90 within the handpiece or probe 46 uses an open-loop control method utilizing an inverse system filter for improving scanning stability and applying the described calibration method. The calibration method of the present invention allows open-loop operation. The method for scanner calibration described herein tunes the parameters of the scanner to give the best performance. The scanner drive circuitry does not need additional feedback signals during operation, thereby dramatically simplifying the scanner and dental OCT system and reducing overall system cost and complexity.

Figure 7:
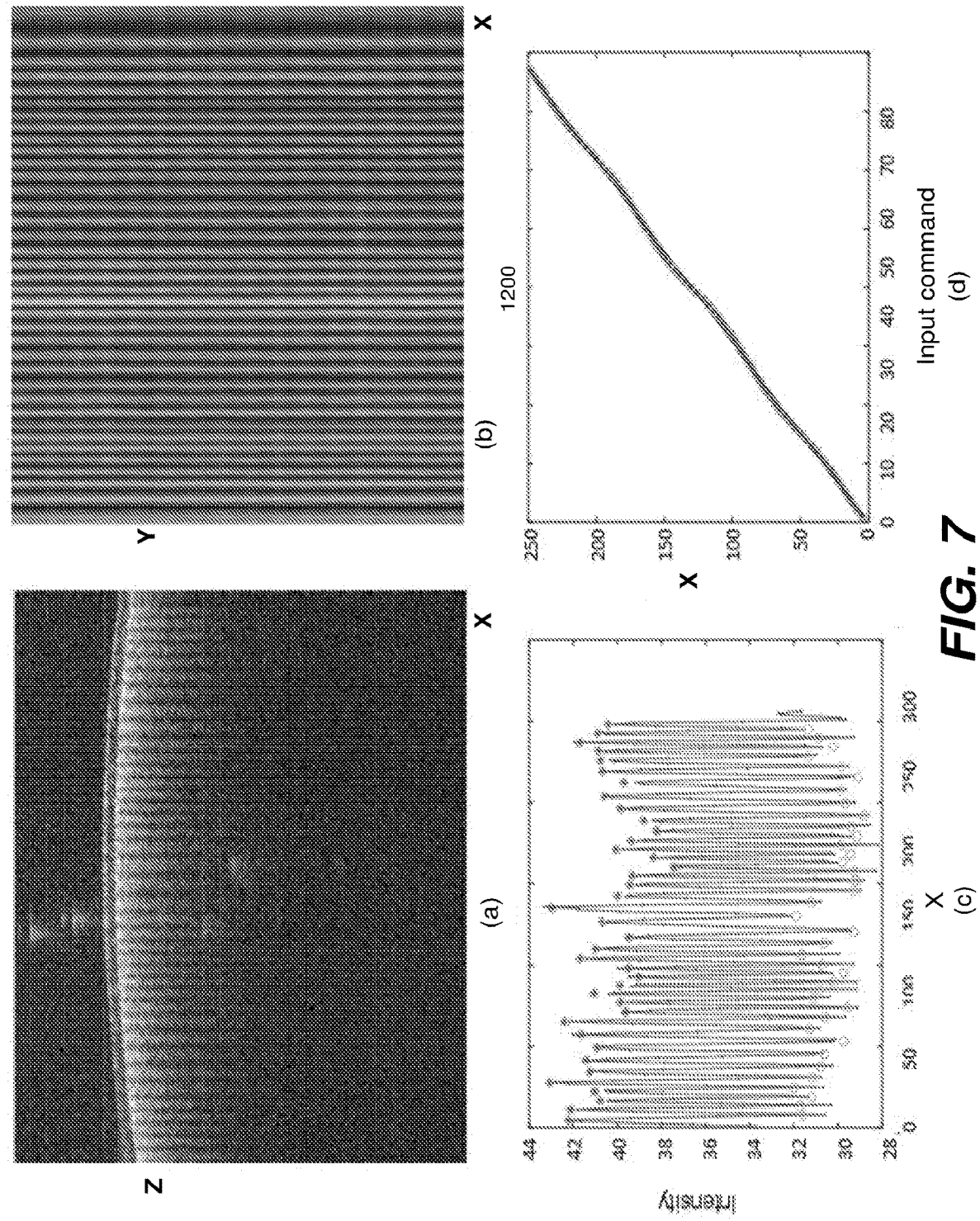
FIG. 7 displays a series of related images acquired using the target of FIG. 4.

As shown in FIG. 4, a grating target 200 is used to provide a reference for the calibration method. Grating target 200 is formed as an arrangement of linear features formed on a flat surface, with paired reflective/scattering and light-absorbing features repeated across the surface. The example embodiment shown in FIG. 4 has repeated alternating reflective and absorbing linear features extending in parallel to provide the grating pattern. The parallel direction of the linear features can be orthogonal to the scanning direction. Measurements at best resolution are obtained with calibration target features orthogonal to the scan direction; in practice, linear features are preferably within a few degrees of orthogonal to the scan direction. Reflective linear features provide diffuse reflection for incident light from probe 46. Alternating features can have a periodic distribution, evenly dimensioned as shown in FIG. 7 part (b) or can be non-periodic.

Overall, the power ratio between light from reflective/scattering features and light measured from absorbing features should be sufficient so that sensing components associated with probe 46 can clearly and unambiguously distinguish the reflective and absorbing features of the calibration target from each other in the returned beam of light obtained from the calibration target surface. What is needed is clear contrast between the alternating features, as sensed by the OCT system. Thus, for highly sensitive detectors, the relative difference in light measured from reflective and light-absorbing features can be slight. In practice, use of lower cost detectors and distinctive target 200 features is preferable.

For example, according to an example embodiment of the present invention, the reflective linear features in the grating pattern can reflect or scatter more than half of the incident scanned light, such as reflecting or scattering 60% or more of the incident scanner beam in an example design; similarly, absorbing features in the grating pattern can absorb more than half of the incident scanned light, such as absorbing 60% or more of the incident scanned light in one example embodiment. The reflected light from the calibration pattern returns along the sample path from probe 46 and is directed to the OCT circuitry for image reconstruction and to generate logic for compensating for scanner inaccuracy.

Feature dimensioning and spacing is sized to measure the response and resolution of the OCT system. According to an exemplary embodiment, feature spacing is at twice the resolution of the system resolution, so that spacing between reflective features is at 20 μm for an OCT system with 10 μm resolution.

Figure 5:
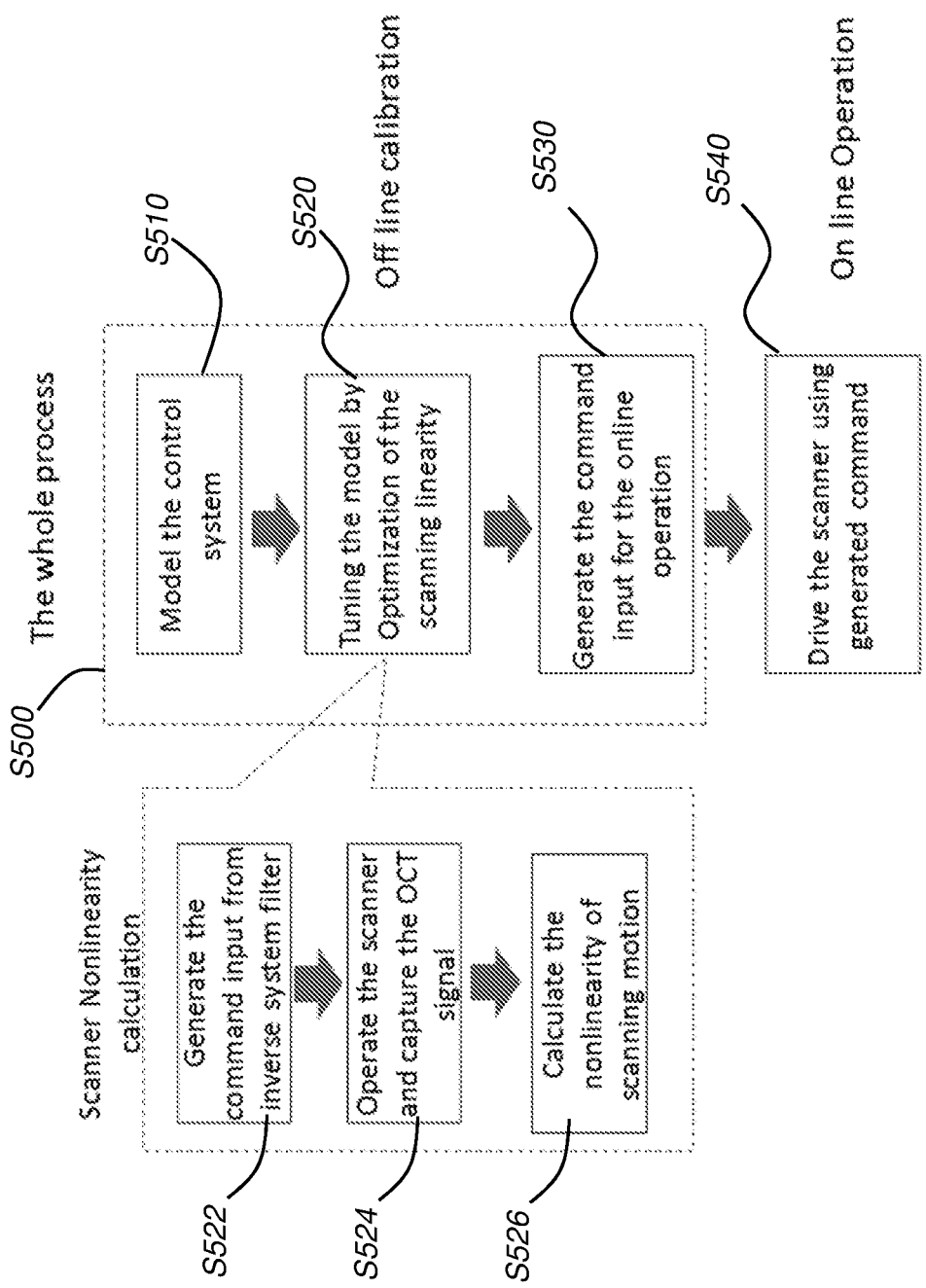
FIG. 5 is a logic flow diagram displaying a calibration process according to an example embodiment of the present invention.

FIG. 5 displays a logic flow diagram representation of a calibration process S500 according to an example embodiment of the present disclosure. In an initial modeling step S510, the scanner's control system is modeled using the following equation:

$$H(s) = K\frac{\omega_n^2}{s^2 + 2\xi\omega_n s + \omega_n^2}$$

wherein:
K is the gain
$\omega_n^2$ is the natural or resonance frequency of the scanner;
s represents the complex Laplace variable; and
ζ is the damping ratio, which is equal to $$\frac{1}{2Q}$$

for the MEMS device.

Due to the high Q-factor of the MEMS-based intraoral scanner, the system can become unstable, particularly when the system frequency is close to the natural frequency ωn for MEMS circuitry. To compensate and provide improved stability, an inverse system filter is applied in a tuning step S520, as shown in the FIG. 5 sequence. An inverse filter command step S522 generates and applies an inverse filter configured to improve scanner stability and designed according to:

$$F(s) = \frac{H^{-1}(s)\omega_1^2}{(s + \omega_1)^2}$$

wherein ω1 is the additional filter pole to make it a realistic system. A capture step S524 and calculation step S526 then follow for applying the inverse filter for imaging the target 200. The results generate command instructions in a command generation step S530. Calibration is then applied for sample acquisition in each subsequent operation step S540.

A value larger than the natural frequency may be chosen for Wi. By applying the inverse filter, the input drive signal to the scanner is the output from the inverse filter. In concept, if the system is correctly modeled, the output of the mirror angle follows the voltage input very well.

However, in practice, the resonant or natural frequency $\omega_n^2$ of the MEMS mirror often varies for different MEMS-based scanners. Even a pre-calibrated $\omega_n^2$ for a specific scanner may not give satisfactory performance due to a number of factors, such as environmental temperature and humidity change, driver setting, and electrical characteristics of the connection cables and connectors. To minimize the effect of such factors, an off-line calibration method is carried out prior to online operation. A goal of this calibration procedure is to minimize the nonlinearity of the scanner by tuning the value $\omega_n^2$, which may be defined as follows:

$$\min_{\omega_n}(N(\omega_n))$$

wherein $N(\omega_n)$ is the scanner nonlinearity defined by the root mean square (RMS) of linear fitting error of the scanning trajectory. In essence, the value $N(\omega_n)$ can be considered as a cost function to be minimized in achieving calibration.

Figure 6:
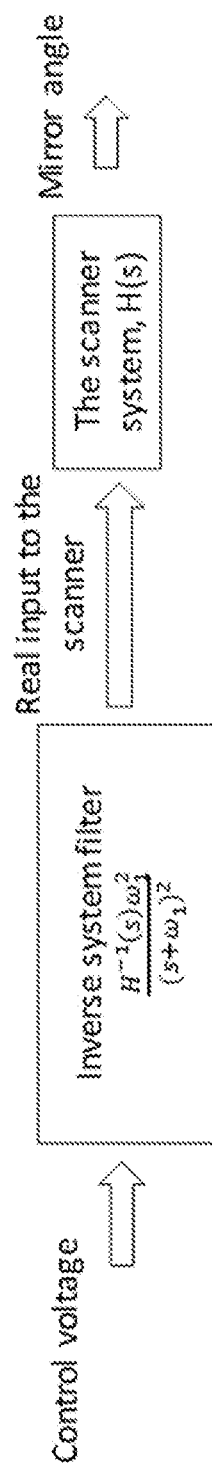
FIG. 6 is a flow diagram displaying a control system model using the inverse system filter generated in the process of FIG. 5.

FIG. 6 is a flow diagram that displays a control system model using the inverse system filter generated in the process given in FIG. 5. The input to the scanner is a drive signal that allows open-loop control of mirror angle, eliminating the need for a control loop with supporting scanner position sensors.

To measure the scanning trajectory, target 200 of FIG. 4 is used. Depending on the absorption of the laser energy, the intensity image can be obtained through the reconstruction of the OCT signal.

The various parts of FIG. 7 display a series of related images acquired using target 200 of FIG. 4. FIG. 7 part (a) shows a portion of a B-scan image, formed as a series of A-scan images of the grating features. After a volume image is obtained, an intensity image of grating features in the X-Y plane can be obtained by averaging the intensity value along the Z-axis direction as shown in FIG. 7 part (b). Then, the data can be further averaged along the Y-axis direction, which gives a one-dimensional (1-D) plot along the scanning direction as shown in FIG. 7 part (c). The averaging process can dramatically reduce the noise in the image. Then, the peak and valley positions along the scanning direction are detected to identify the points highlighted in FIG. 7 part (c). A linear fitting is applied along the scanning direction as shown in FIG. 7 part (d). The final nonlinearity of the scanner is calculated in terms of RMS of fitting error. As can be seen from FIG. 7 part (d), there can be a significant amount of ringing effect in the trajectory.

Figure 8:
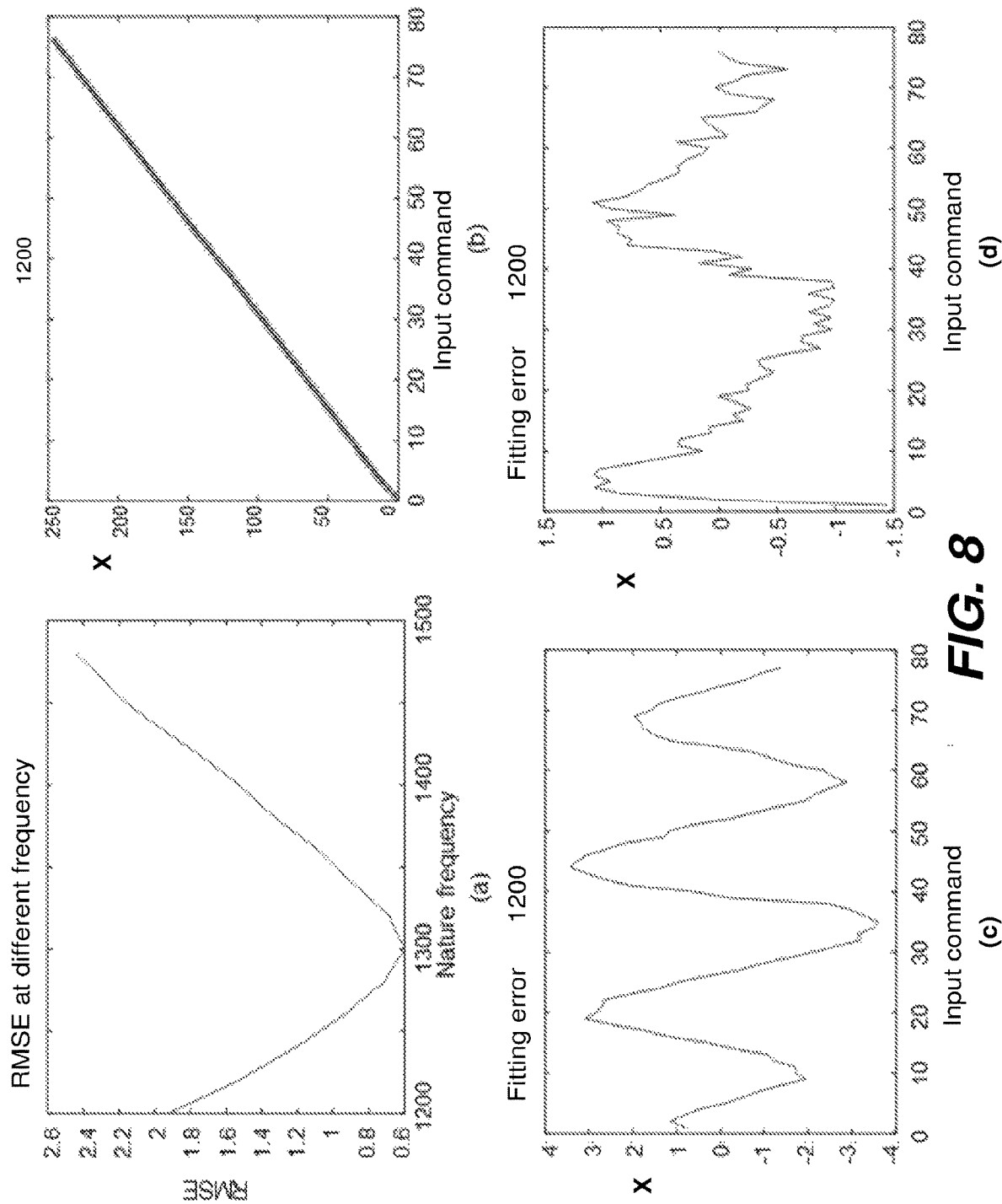
FIG. 8 displays exemplary data resulting from calibration target measurement.

FIG. 8 displays example data resulting from target measurement. The RMS of the fitting error at different frequencies is shown in FIG. 8 part (a). The trajectory of the beam along the x-axis, at the optimal natural frequency, is shown in FIG. 8 part (b). The optimal natural frequency $\omega_n$ for the scanning mirror in this case is 1.3 KHz.

Figure 9:
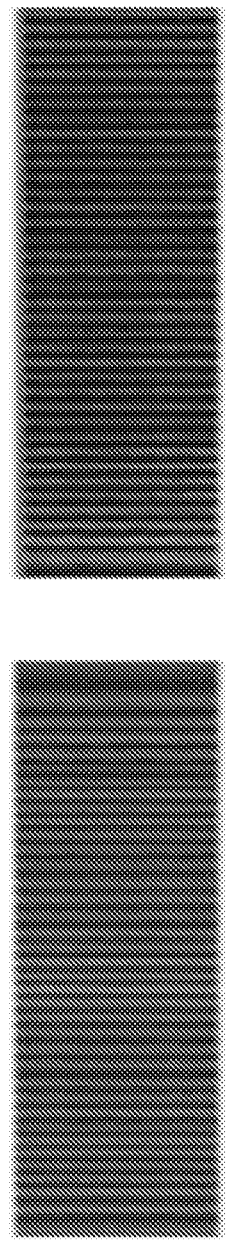
FIG. 9 displays images obtained from the target.

Referring to the FIG. 8 sequence, comparison of the trajectory between 1.2 KHz and 1.3 KHz natural frequencies in part (a) shows that the higher frequency gives much better linearity. The scanner nonlinearity is reduced by a factor of 3. The linear fitting error of 1.2 KHz and 1.3 KHz natural frequencies is shown graphically in FIG. 8 parts (c) and (d), respectively, with ordinate (vertical) axis values shown at different scales. The peak-values of the fitting errors are also reduced by a factor of about 3 when using 1.3 KHz natural frequency in the model. In the images acquired from the calibration grating target 200, the lines are distributed more evenly for the optimal natural frequency at 1.3 KHz as shown, respectively, in FIG. 9 part (a) for 1.2 KHz and in FIG. 9 part (b) for 1.3 KHz.

After optimization of the system model, software instructions can be generated, with tuned values for online operation. The open-loop control mode can then be applied during online operation. Therefore, no additional sensors are needed for control and feedback related to scanning. Operating in an open-loop manner thus simplifies system design and operation. Since the calibration method described herein only requires a grating target, the method can be readily performed, periodically, as well as whenever environmental conditions or hardware setup are altered.

According to an alternate example embodiment, target 200 is provided to the OCT user for on-site calibration. Supporting firmware can be provided for a self-calibration or calibration check-and-adjust function executed by the end-user, such as with command display and entry using display 72 (FIG. 1) for example. Using target 200 in this way allows periodic re-calibration by the end-user, such as once a month, for example.

The invention has been described in detail with particular reference to a presently understood example embodiments, but it will be understood that variations and modifications can be affected within the spirit and scope of the invention. For example, control logic processor 70 can be any of a number of types of logic processing device, including a computer or computer workstation, a dedicated host processor, a microprocessor, logic array, or other device that executes stored program logic instructions. The presently disclosed example embodiments are therefore considered in all respects to be illustrative and not restrictive. The scope of the invention is indicated by the appended claims, and all changes that come within the meaning and range of equivalents thereof are intended to be embraced therein.

Consistent with at least one example embodiment, example methods/apparatus can use a computer program with stored instructions that perform on image data that is accessed from an electronic memory. As can be appreciated by those skilled in the image processing arts, a computer program of an example embodiment herein can be utilized by a suitable, general-purpose computer system, such as a personal computer or workstation. However, many other types of computer systems can be used to execute the computer program of described example embodiments, including an arrangement of one or networked processors, for example.

A computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and/or processes that are well known. It will be further understood that exemplary computer program product embodiments herein may embody algorithms and/or processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the present invention may have been disclosed herein with respect to only one of several implementations/example embodiments, such feature can be combined with one or more other features of the other implementations/example embodiments as can be desired and advantageous for any given or particular function. The term "a" or "at least one of" is used to mean one or more of the listed items can be selected. The term "about" indicates that the value listed can be somewhat altered, as long as the alteration does not result in nonconformance of the process or structure to the illustrated example embodiment. Other embodiments of the invention will become apparent to those skilled in the art from consideration of the specification and practice of the invention disclosed herein. It is intended that the specification and examples be considered as exemplary only, with a true scope and spirit of the invention being indicated by the following claims.

What is claimed is:

1. An intraoral scanner for use with a dental optical coherence tomography system, the intraoral scanner comprising:
a scanning reflector that is energizable to direct a scanning beam toward a surface in a raster pattern, wherein the scanning reflector further directs a reflected beam from the surface toward a detector wherein the detector is in signal communication with a processor configured for calibrating the detector to detect variations in the reflected beam from a sample target, and
wherein the scanning reflector is calibrated to direct the scanning beam and the reflected beam in an open-loop control mode through calculation of a scanner nonlinearity by the processor according to a linear fitting error of a measured scanning trajectory determined using optical coherence tomography images of the sample target, wherein the scanning reflector is configured to operate at a natural frequency determined based at least in part on the calculated scanner nonlinearity.

2. The intraoral scanner of claim 1, wherein the raster pattern disposes the scanning beam to discrete, uniformly spaced positions along the surface.

3. The intraoral scanner of claim 1, wherein the scanning reflector is a micro-electromechanical systems (MEMS) device.

4. The intraoral scanner of claim 1, wherein the scanning reflector further has an inverse system filter that is configured to improve stability of the scanning reflector.

5. A dental optical coherence tomography system, comprising:
an intraoral probe having:
(a) a micro-electromechanical scanning reflector that is energizable to direct a scanning beam, in a raster pattern, toward a scanned sample surface, wherein the micro-electromechanical scanning reflector further redirects reflected light from the scanned sample surface toward a detector, wherein the micro-electromechanical scanning reflector is calibrated to direct the scanning beam and a reflected beam in an open-loop control mode; and
(b) a processor employing control logic that is in signal communication with the detector and that is configured to provide a raster drive signal to the micro-electromechanical scanning reflector that directs the scanning beam toward spaced-apart positions along the sample surface according to a calibration pattern previously sensed by the detector, wherein the calibration pattern has a sequence of alternating reflective and absorbing features, and the processor further employing control logic to tune a natural frequency of the micro-electromechanical scanning reflector to reduce nonlinearity.

6. The dental optical coherence tomography system of claim 5, wherein the calibration pattern of alternating reflective and absorbing features has a periodic distribution.

7. The dental optical coherence tomography system of claim 5, wherein the processor employing control logic is further conditioned by an inverse filter generated to improve scanning stability.

8. The dental optical coherence tomography system of claim 5, wherein the raster drive signal provides open-loop control of the micro-electromechanical scanning reflector.

9. The dental optical coherence tomography system of claim 5, wherein the intraoral probe further comprises a time-domain dental optical coherence tomography system.

10. The dental optical coherence tomography system of claim 5, wherein the intraoral probe further comprises a spectrum-domain dental optical coherence tomography system.

11. The dental optical coherence tomography system of claim 5, wherein the intraoral probe further comprises a swept-source dental optical coherence tomography system.

12. A method for calibration of a scanning reflector in a dental optical coherence tomography system, the method comprising steps of:

scanning a light along a calibration target using a scanning reflector, wherein the calibration target has a plurality of target features, and wherein the target features are paired and the target features in each pair alternate between a light-absorbing feature and a reflective or scattering feature;

correcting for scanner nonlinearity by tuning one or more scanning reflector parameters according to a natural frequency of the scanning reflector;

calibrating the scanning reflector to direct scanning beams and reflected beams in an open-loop control mode; and optimizing a cost function defined by a linear fitting error of a measured scanning trajectory determined using optical coherence tomography images of the scanned calibration target.

13. The method of claim 12, wherein the method further comprises a step of operating the scanning reflector according to a natural frequency calculated in optimizing the cost function.

14. The method of claim 12, wherein the scanning is providing time-domain dental optical coherence tomography.

15. The method of claim 12, wherein the scanning is providing spectrum-domain dental optical coherence tomography.

16. The method of claim 12, wherein the scanning is providing swept-source dental optical coherence tomography.

17. The method of claim 12, wherein the alternating light-absorbing and reflective or scattering features of the calibration target are extended in parallel to each other.

* * * * *